(12) United States Patent
Ward et al.

(10) Patent No.: US 10,653,850 B2
(45) Date of Patent: May 19, 2020

(54) BOOT REMOVER (71) Applicant: Sanofi-Aventis Deutschland GmbH, Frankfurt am Main (DE)

(72) Inventors: Chris Ward, Dennbigshire (GB); Gareth Roberts, Wrexham (GB); Graham Wilson, Flintshire (GB); Troy Baker, Denbighshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 400 days.

(21) Appl. No.: 15/037,900

(22) PCT Filed: Nov. 25, 2014

(86) PCT No.: PCT/EP2014/075556
§ 371 (c)(1),
(2) Date: May 19, 2016

(87) PCT Pub. No.: WO2015/078867
PCT Pub. Date: Jun. 4, 2015

(65) Prior Publication Data
US 2016/0375199 A1 Dec. 29, 2016

(30) Foreign Application Priority Data
Nov. 28, 2013 (EP) .................................. 13194892

(51) Int. Cl.
*A61M 5/32* (2006.01)
*A61M 5/00* (2006.01)

(52) U.S. Cl.
CPC .......... *A61M 5/3204* (2013.01); *A61M 5/002* (2013.01); *A61M 5/3202* (2013.01);
(Continued)

(58) Field of Classification Search
CPC .. A61M 2005/3247; A61M 2005/3267; A61M 5/002; A61M 5/3202; A61M 5/3204; A61M 5/326
See application file for complete search history.

(56) References Cited

U.S. PATENT DOCUMENTS

| 4,106,621 A | 8/1978 | Sorenson |
| 4,420,085 A | 12/1983 | Wilson et al. |
| 2014/0224688 A1* | 8/2014 | Slemmen .............. A61M 5/002 206/365 |

FOREIGN PATENT DOCUMENTS

| EP | 2574355 | * 3/2013 | ............. A61M 5/00 |
| EP | 2574355 | 4/2013 | |

(Continued)

OTHER PUBLICATIONS

International Search Report and Written Opinion in International Application No. PCT/EP2014/075556, dated Jan. 30, 2015, 9 pages.
(Continued)

Primary Examiner — Brandy S Lee
(74) Attorney, Agent, or Firm — Fish & Richardson P.C.

(57) ABSTRACT

The invention relates to a boot remover (10) for removing a protective needle boot (11) from a drug delivery device (1), wherein the boot remover (10) is arranged to engage the protective needle boot (11) when attached to the drug delivery device (1), wherein the boot remover (10) comprises a tab (10.2) extending in a distal direction (D), wherein the tab (10.2) is engageable to a packaging (13) of the drug delivery device (1). Furthermore, the invention relates to a drug delivery arrangement comprising a drug delivery device (1), a packaging (13) and the boot remover (10).

12 Claims, 5 Drawing Sheets
Specification includes a Sequence Listing.

(52) U.S. Cl.
CPC ..... *A61M 5/326* (2013.01); *A61M 2005/3247* (2013.01); *A61M 2005/3267* (2013.01)

(56) References Cited

FOREIGN PATENT DOCUMENTS

| | | |
|---|---|---|
| JP | H10-5333 | 1/1998 |
| JP | 2013-524916 | 6/2013 |
| WO | WO 2011/131996 | 10/2011 |

OTHER PUBLICATIONS

International Preliminary Report on Patentability in International Application No. PCT/EP2014/075556, dated May 31, 2016, 9 pages.
Rote Liste, "50. Hypophysen-, Hypothalamushormone, andere regulatorische Peptide u. ihre Hemmstoffe," Chapter 50, ed. 2008, 20 pages.

\* cited by examiner

BOOT REMOVER

CROSS-REFERENCE TO RELATED APPLICATIONS

This application is a U.S. national stage application under 35 USC § 371 of International Application No. PCT/EP2014/075556, filed on Nov. 25, 2014, which claims priority to European Patent Application No. 13194892.9, filed on Nov. 28, 2013, the entire contents of which are incorporated herein by reference.

TECHNICAL FIELD

The present invention relates to a boot remover for removing a protective needle boot from a drug delivery device. the invention relates to a drug delivery arrangement comprising a drug delivery device, a packaging and the boot remover.

BACKGROUND OF THE INVENTION

Pre-filled syringes that are filled with a selected dosage of a medicament are well known injection devices for administering the medicament to a patient. Drug delivery devices comprising a needle shield for covering a needle of a pre-filled syringe before and after use are also well known. Typically, the needle shield is either manually moved or moved by the action of a relaxing spring to surround the needle.

A different type of drug delivery device known in the state of the art solves the object of providing needle safety by arranging the pre-filled syringe movable relative to a body, whereas the pre-filled syringe is retracted into the body after the injection.

SUMMARY OF THE INVENTION

Certain aspects of the invention relate to an improved boot remover.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient.

Respectively, the proximal end of an element or the proximal direction is directed away from the body of the patient receiving the injection and opposite to the distal end or distal direction.

According to the invention a boot remover is provided for removing a protective needle boot from a drug delivery device, wherein the boot remover is arranged to engage the protective needle boot when attached to the drug delivery device, wherein the boot remover comprises a tab extending in a distal direction, wherein the tab is engageable to a packaging of the drug delivery device.

The boot remover may be applied with a drug delivery arrangement comprising:
- a drug delivery device for dispensing a dose of a drug, comprising:
  - a support body having a first end defining a first opening and a second end defining a second opening,
  - a syringe barrel sealed by a stopper slidably disposed therein along an axial direction and adapted to have an integrated needle or to be coupled with a needle assembly comprising a needle, wherein the syringe barrel is positioned within the support body,
  - a protective needle boot arrangeable over the needle on the syringe barrel,
  - a needle shield adapted to be coupled to one of the ends of the support body and slidably disposed thereon for covering or exposing the needle; and
- a boot remover, e.g. arrangeable over the needle shield to receive and substantially cover the needle shield, wherein the boot remover is arranged to engage the protective needle boot, and
- a packaging for retaining the drug delivery device, wherein the packaging is arranged to allow gripping a part of the drug delivery device proximally from the needle shield whilst preventing access to the needle shield.

The boot remover and the package prevent a user from holding the needle shield such that the support body cannot be moved in a distal direction with respect to the needle shield prior to removal of the boot remover and the protective needle boot. Hence, as the user must hold the support body the syringe barrel and the support body remain in place relative to the needle shield. The protective needle boot is thus removed without prematurely exposing the needle.

In an exemplary embodiment the tab is attachable to the packaging by a mechanical fixing and/or by an adhesive bond.

Likewise, the tab may be integrally shaped with the packaging.

In an exemplary embodiment the boot remover may be substantially cylindrical for abutting and/or retaining the protective needle boot. The boot remover may be arranged to engage the protective needle boot by friction and/or by at least one barb engageable in a recess or behind a shoulder on the protective needle boot.

In another exemplary embodiment the boot remover may be arranged as a rigid outer part of a two-part protective needle boot with a soft inner part and a rigid outer part. Likewise the boot remover may be integrally shaped with the protective needle boot.

The boot remover may preferably comprise a plastic material that is flexible enough to deform through a minimum of 90° during the removal of the drug delivery device from the packaging.

Likewise, this flexibility may be provided by a transversally arranged live hinge for allowing a proximal end of the drug delivery device to be lifted out of the packaging while the tab is connected to the packaging.

In an exemplary embodiment the tab may comprise a distal end part with an increased width for engaging a in a front clearance distally from a constriction in the packaging thus allowing the drug delivery device with the boot remover to be laterally inserted into the packaging but to retain the boot remover in the packaging when the drug delivery device is pulled substantially in the proximal direction thus removing the protective needle boot from the needle. The front clearance in the packaging may comprise a back taper for preventing the tab from slipping sideways out of the front clearance.

The packaging may comprise a deep-drawn rigid or flexible material.

In one embodiment the packaging is shaped substantially corresponding to the drug delivery device with a rear clearance allowing to grip a part of the drug delivery device proximally from the needle shield, e.g. the support body or an outer body telescoped with the support body and coupled to the stopper through a plunger, whilst preventing access to the needle shield.

In another exemplary embodiment the packaging comprises a flexible material and is arranged as a blister pack, wherein the tab of the boot remover is fixed to a distal end of the packaging.

The packaging may comprise a predetermined breaking point facilitating the packaging to be torn apart allowing to grip a part of the drug delivery device proximally from the needle shield, e.g. the support body or an outer body telescoped with the support body and coupled to the stopper through a plunger, whilst preventing access to the needle shield.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION OF PREFERRED EMBODIMENTS

Figure 1:
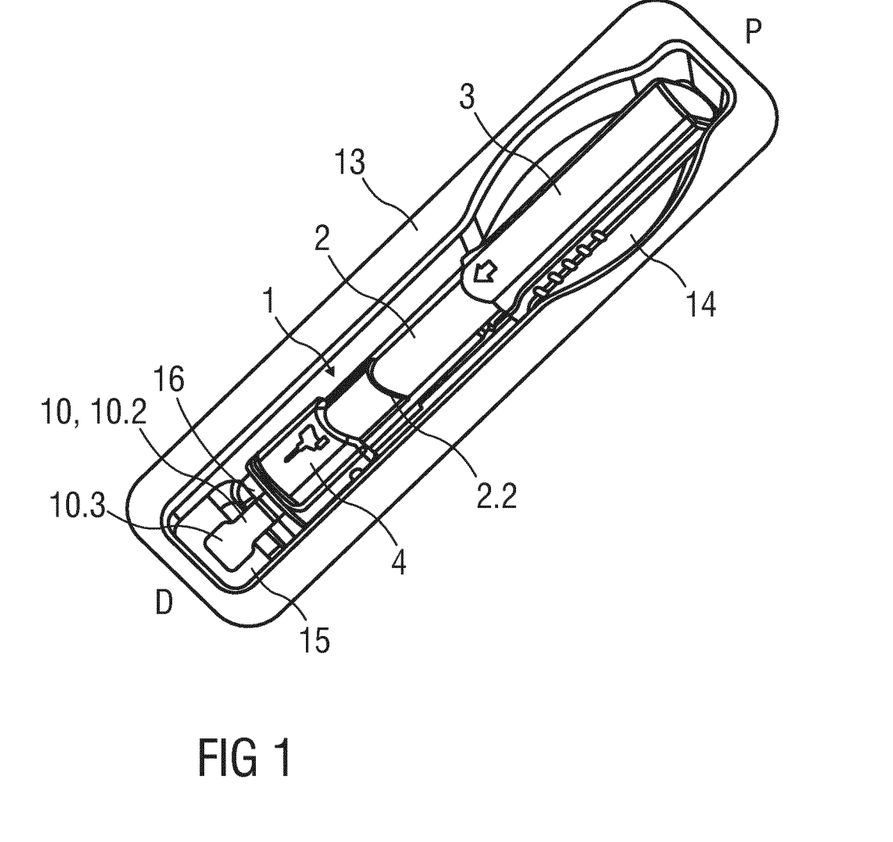
FIG. 1 is a schematic perspective view of a drug delivery device comprising a support body, an outer body and a needle shield in an initial state arranged in a packaging.

FIG. 1 is a perspective view of a drug delivery device 1 comprising a support body 2, an outer body 3 and a needle shield 4, all of them having an essentially tubular shape.

Figure 2:
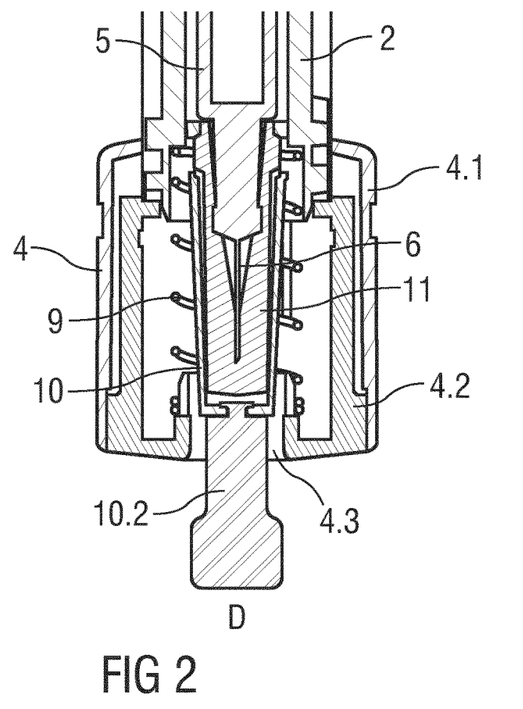
FIG. 2 is a detail longitudinal section of the drug delivery device.

FIG. 2 is a detail longitudinal section of the drug delivery device 1. A proximal end of the support body 2 is telescoped in the outer body 3 and a distal end of the support body 2 is telescoped in the needle shield 4. A syringe barrel 5 is slidably arranged within the support body 2, the syringe barrel 5 defining an inner cavity for a dose of a drug. A hollow injection needle 6 is arranged on a distal end of the syringe barrel 5. A stopper (not illustrated) is slidably arranged within the syringe barrel 5 for sealing its proximal end and for displacing the drug from the syringe barrel 5 through the injection needle 6. A plunger rod (not illustrated) is arranged within the outer body 2 for engaging the stopper. The plunger rod may be screwed or snapped into the stopper. A needle shield spring 9 is arranged for biasing the needle shield 4 in the distal direction D against the support body 2.

The outer body 3 is movable in a distal direction D and in a proximal direction P with respect to the support body 2.

The syringe barrel 5 is inserted into the support body 2. The syringe barrel 5 abuts the support body 2 so that the syringe barrel 5 is fixed towards the distal direction D in its axial position with respect to the support body 2. This may be achieved by a finger flange on the syringe barrel 5 abutting a rib in the support body 2.

The support body 2 comprises an indicator ring 2.2 in the shape of radially outwards protruding and essentially circumferential rib. The indicator ring 2.2 may cover part of or the whole circumference of the support body 2. The indicator ring 2.2 is arranged to interact with the needle shield 4 so as to limit distal movement of the support body 2 with respect to the needle shield 4. Furthermore, the support body 2 comprises a locking mechanism and linear guide rails that run in an axial direction for providing a staged movement between the support body 2, the outer body 3 and the needle shield 4.

The needle shield 4 comprises a tubular body section 4.1 and a cap part 4.2 with a central opening 4.3. The cap part 4.2 is engaged to the body section 4.1 by a snap fit (not illustrated) thus preventing relative axial movement. A protective needle boot 11 may be positioned over the needle 6 on the syringe barrel 5 in and/or through the central opening 4.3 of the cap part 4.2 before and after an injection. The cap part 4.2 is rotationally locked to the body section 4.1. This may be achieved by the cap part 4.2 having a non-circular, e.g. elliptical cross section engaging in a corresponding opening in the body section 4.1.

A boot remover 10 is arranged for removing the protective needle boot 11 prior to an injection. The boot remover 10 may be arranged to engage the needle boot 11 by friction or by means of barbs. The boot remover 10 comprises a tab 10.2 extending from the opening 4.3 for facilitating boot removal. Likewise the boot remover 10 may be arranged as a tab 10.2 integrally shaped with the protective needle boot 11.

In an initial state the drug delivery device 1 is retained in a packaging 13, which may comprise a deep-drawn rigid or flexible material, e.g. a plastic material. The tab 10.2 is attached to the packaging 13 by a mechanical fixing such as a positive and/or non-positive lock and/or by an adhesive bond, like heat adhesion or solvent adhesion. Likewise, the tab 10.2 may be integrally shaped with the packaging 13.

Figure 3:
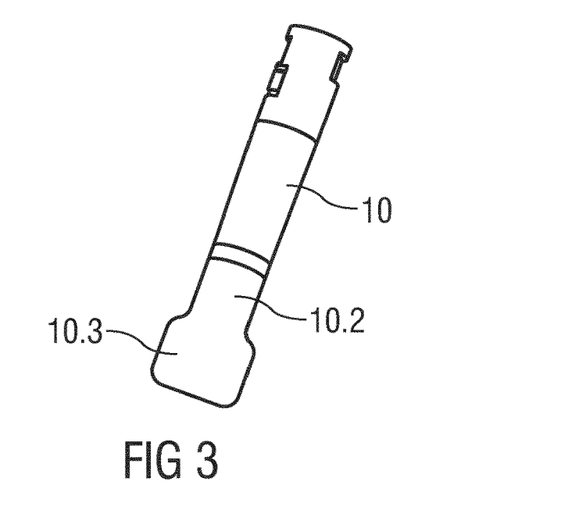
FIG. 3 is a schematic perspective view of a boot remover.

FIG. 3 is a perspective view of the boot remover 10.

In the illustrated embodiment the boot remover 10 is substantially cylindrical for abutting and/or retaining the protective needle boot 11. Likewise, the boot remover 10 may replace a rigid outer part of a two-part protective needle boot 11 with a soft inner part and a rigid outer part. The tab 10.2 is arranged as a distal extension to the boot remover 10 with a predominantly flat shape. The cross sectional geometry of the tab 10.2 is largely dependant on the intended fixing to the packaging 13. The boot remover 10 may preferably comprise a plastic material that is flexible enough to deform through a minimum of 90° during the removal of the drug delivery device 1 from the packaging 13. In the illustrated embodiment the tab 10.2 comprises a distal end part 10.3 with an increased width which may be held in a front clearance 15 distally from a constriction 16 in the packaging 13 restricting movement of the tab 10.2 in the proximal direction P.

Figure 7:
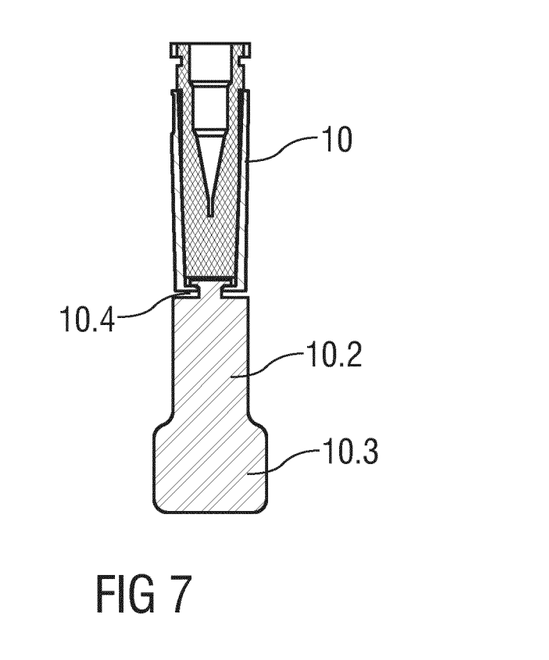
FIG. 7 is a schematic perspective view of an embodiment of the boot remover.

Flexibility of the tab 10.2 can likewise be provided by a live hinge 10.4 as in the exemplary embodiment of the boot remover 10 illustrated in FIG. 7.

The packaging 13 is shaped substantially corresponding to the drug delivery device 1 with a rear clearance 14 allowing a user to grip the outer body 3 while making it difficult to grip the support body 2 or, more importantly, the needle shield 4.

FIGS. 1 and 2 show the drug delivery device 1 prior to an injection. The outer body 3 is fully extended in the proximal direction P from the support body 2. The needle shield 4 is fully extended from the support body 2 in the distal direction D. The injection needle 6 is in a retracted position within the needle shield 4. The needle shield spring 9 is relaxed.

Figure 4:
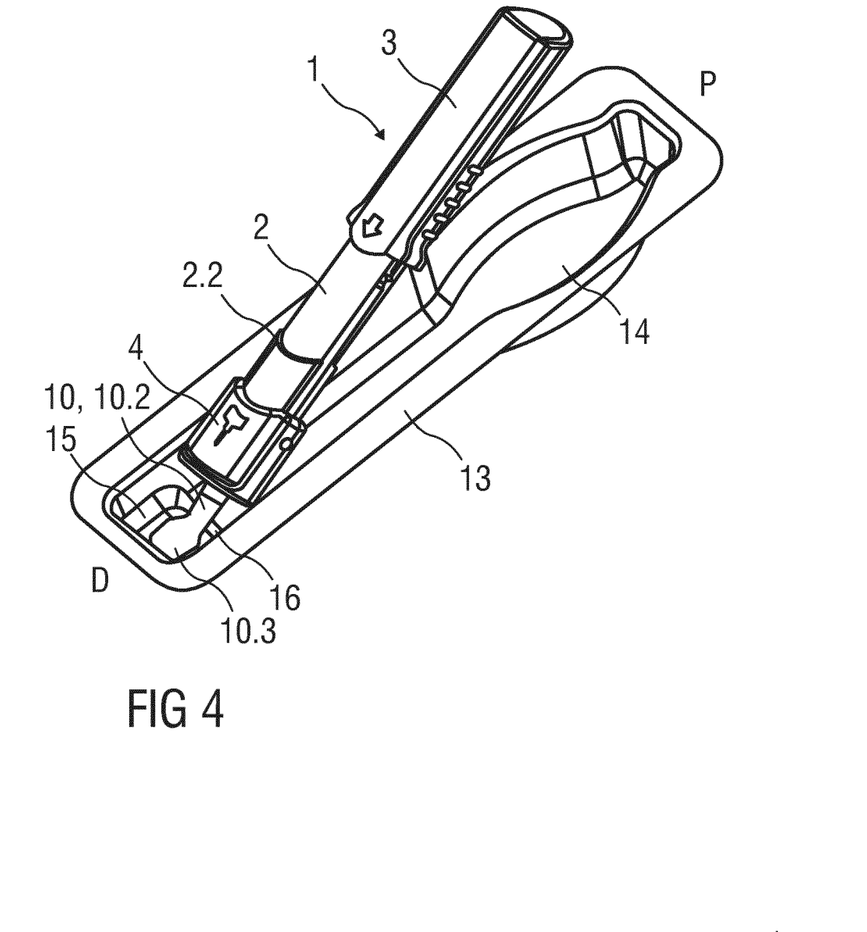
FIG. 4 is a schematic perspective view of the drug delivery device with its proximal end being lifted from the packaging.
Figure 5:
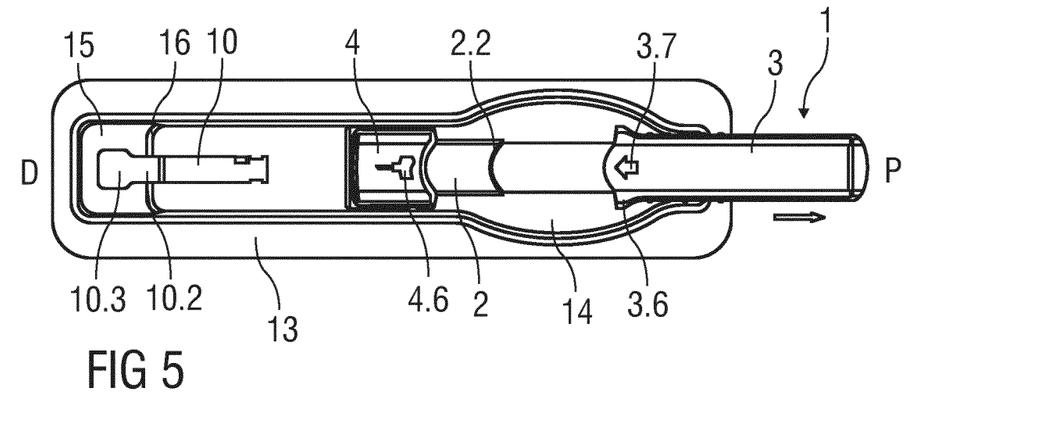
FIG. 5 is a schematic perspective view of the drug delivery device being pulled out of the packaging.

A user may grab the packaging 13 with one hand and the outer body 3 with the other hand, lift the outer body 3 out of the rear recess 14 (cf. FIG. 4) and pull the outer body 3 in the proximal direction P relative to the packaging 13 (cf. FIG. 5). As the tab 10.2 is fixed to the packaging 13 the boot remover 10 and the protective needle boot 11 remain in position relative to the packaging 13 and are hence removed from the drug delivery device 1 through the central opening 4.3 of the needle shield 4. The protective needle boot 11 is thus removed without exposing the needle 6.

Figure 6:
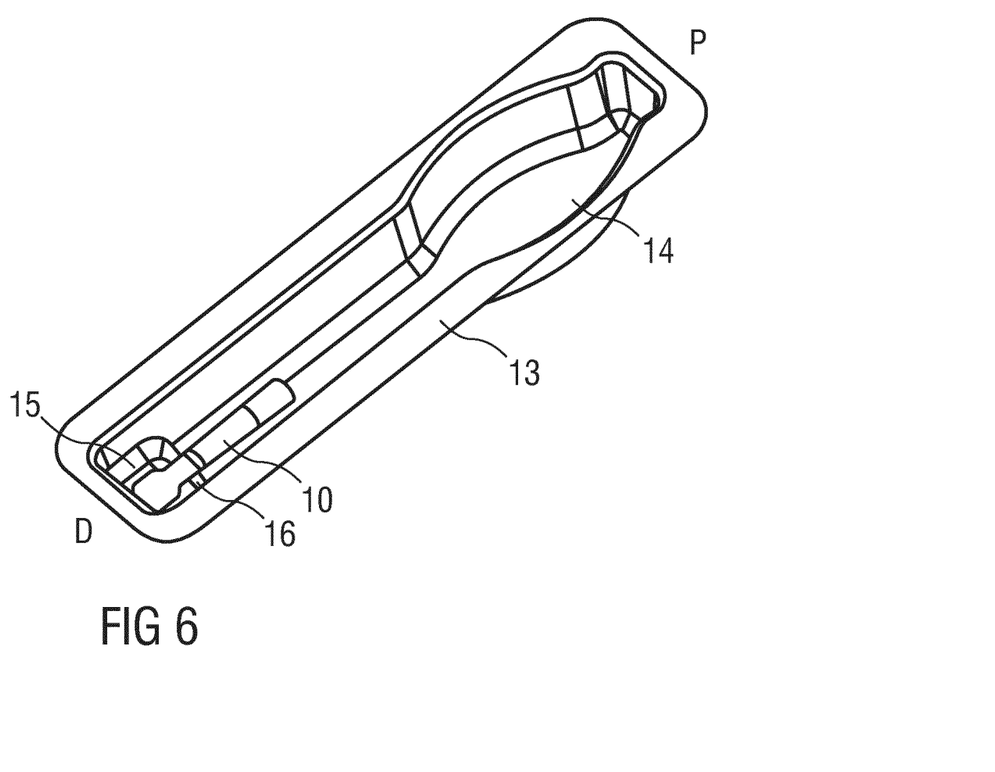
FIG. 6 is a schematic perspective view of the packaging with the boot remover after removal of the drug delivery device.

FIG. 6 is a perspective view of the packaging 13 with the boot remover 10 after removal of the drug delivery device 1.

The user may now push the distal end of the needle shield 4 against an injection site, e.g. a patient's skin. The force from the user's hand is resolved through the outer body 3, the support body 2, into the needle shield 4. As the user applies a sufficiently high force the needle shield 4 is moved in the proximal direction P with respect to the support body 2 and all other parts of the drug delivery device 1 thereby also compressing the needle shield spring 9.

On application of the drug delivery device 1 against the patient's skin the needle shield 4 moves prior to the outer body 3 relative to the support body 2 due to a locking mechanism or detent (not illustrated) between the support body 2 and the outer body 3. This movement is opposed by the friction force of the injection needle 6 when penetrating the skin. In order to avoid a so called wet injection with drug leaking out of the tip of the needle 6 during needle insertion before reaching the insertion depth the friction force of the needle 6 must be less than the counteracting force of the stopper 7 due to friction between the stopper 7 and the inner wall of the syringe 5 and due to the hydrostatic resistance of the drug to be displaced through the hollow needle 6, which depends on the inner diameter of the needle 6 and the viscosity of the drug. The needle insertion depth is defined by the needle shield 4 abutting the indicator ring 2.2. The mating surfaces of the indicator ring 2.2 and the needle shield 4 visually and haptically indicate to the user that they are intended to be pushed completely together in order to correctly apply the drug delivery device 1.

Once insertion depth has been reached, further application of force onto the outer body 3 overcomes the detent so that the outer body 3 decouples from the support body 2 and moves relative to the support body 2 in the distal direction D thus also moving the stopper within the syringe barrel 5 so that the drug is displaced from the cavity through the injection needle 6. Near the end of the injection the stopper bottoms out in the syringe barrel 5. At the same time the outer body 3 abuts the indicator ring 2.2. The mating surfaces of the indicator ring 2.2 and the outer body 3 visually and haptically indicate to the user that they are intended to be pushed completely together in order to correctly apply the drug delivery device 1.

If the user removes the drug delivery device 1 from the injection site the needle shield 4 is no longer pushed against the skin and is hence extended in the distal direction D relative to the other components of the drug delivery device 1 by the needle shield spring 9 such that the injection needle 6 arrives fully inside the needle shield 4. A locking mechanism may be provided between the needle shield 4 and the support body 2 for preventing the needle shield 4 from being retracted once more.

The end of the outer body 3 coupled to the support body 2 may comprise a radially outwards directed flange 3.6 thus improving ergonomics when applying the drug delivery device 1 (cf. FIG. 5).

In an exemplary embodiment a direction indicator 3.7 designed as a profiled cavity or concavity in the surface of the outer body 3 is arranged in the range of the flange 3.6 (cf. FIG. 5).

The needle shield 4 may likewise comprise a direction indicator 4.6 (cf. FIG. 5).

A label retaining recess may be arranged in the outer body 3 for receiving a label which may be customized to the drug to be delivered and/or to the provider of the drug.

Figure 8:
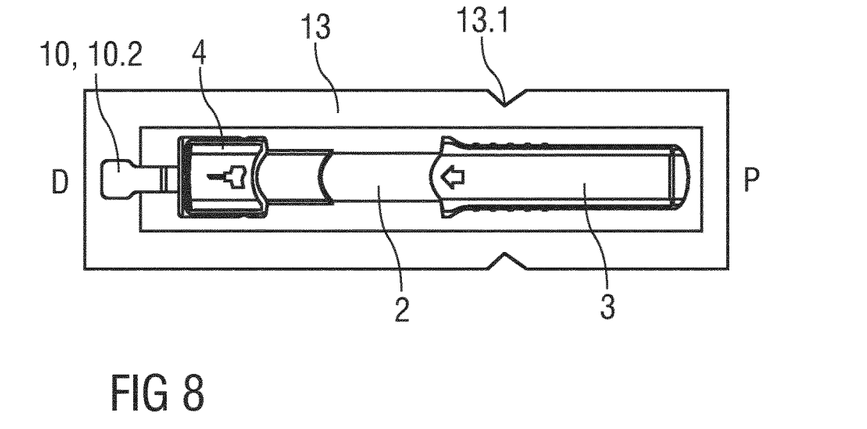
FIG. 8 is a schematic view of the drug delivery device in a non-rigid, flexible packaging in an initial state.
Figure 9:
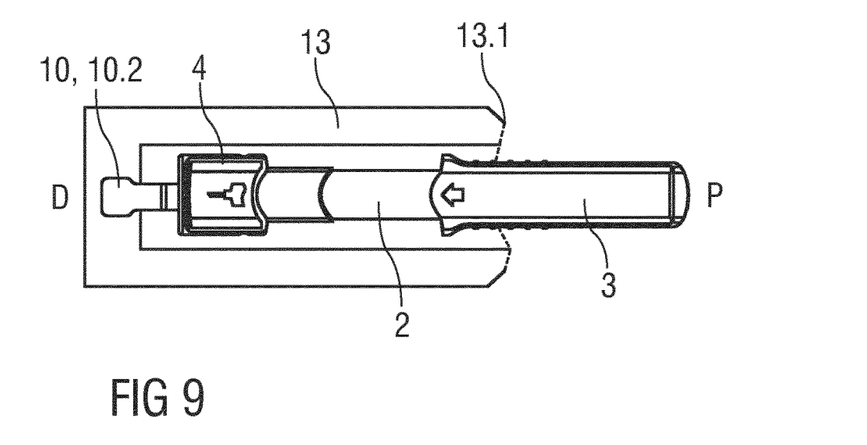
FIG. 9 is a schematic view of the drug delivery device with the flexible packaging being torn apart at a predetermined breaking point.

FIG. 8 is a schematic view of the drug delivery device 1 in an alternative embodiment of the packaging 13. As opposed to the deep-drawn and more rigid packaging of the previous embodiment the packaging 13 of FIG. 8 is a non-rigid, rather flexible packaging 13 in the manner of a blister pack. The tab 10.2 of the boot remover 10 is fixed to one end of the packaging 13. The packaging 13 comprises a predetermined breaking point 13.1 at which the packaging 13 may be torn apart by the user thus arriving in a state as illustrated in FIG. 9. The predetermined breaking point 13.1 is arranged such that the user can grip the outer body 3 or support body 2 but is prevented from gripping the needle shield 4.

Figure 10:
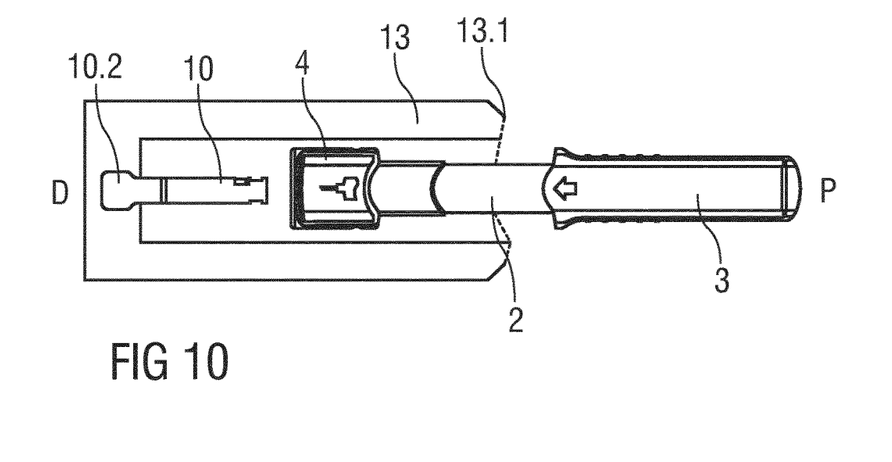
FIG. 10 is a schematic view of the drug delivery device being pulled out of the packaging, wherein the boot remover and the protective needle boot remain in the packaging.

The user may now grab the packaging 13 with one hand and the outer body 3 with the other hand and pull the outer body 3 in the proximal direction P relative to the packaging 13. As the tab 10.2 is fixed to the packaging 13 the boot remover 10 and the protective needle boot 11 remain in position relative to the packaging 13 and are hence removed from the drug delivery device 1 through the central opening 4.3 of the needle shield 4. The protective needle boot 11 is thus removed without exposing the needle 6. FIG. 10 shows the drug delivery device 1 pulled out of the packaging 13. The boot remover 10 and the protective needle boot 11 remain in the packaging 13.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(w-carboxyheptadecanoyl)-des(B30) human insulin and B29-N-(w-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2 (SEQ ID NO:1).

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(02)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(02)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(02)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(02)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(02)25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

LIST OF REFERENCES 1 drug delivery device
2 support body
2.2 indicator ring
3 outer body
3.6 flange
3.7 direction indicator
4 needle shield
4.1 body section
4.2 cap part
4.3 central opening
4.6 direction indicator
5 syringe barrel
6 needle
9 needle shield spring
10 boot remover
10.1 direction indicator
10.2 tab
10.3 distal end part 10.4 live hinge
11 protective needle boot
13 packaging
13.1 predetermined breaking point
14 rear clearance
15 front clearance
16 constriction
D distal direction
P proximal direction

The invention claimed is:

1. A boot remover for removing a protective needle boot from a drug delivery device, the boot remover is configured to engage the protective needle boot when the boot remover is attached to the drug delivery device, wherein the boot remover comprises a tab extending in a distal direction, wherein the tab is integrally shaped with a packaging of the drug delivery device, and the boot remover is matingly engaged with the protective needle boot;
wherein the tab comprises a transversally arranged live hinge such that a proximal end of the drug delivery device is configured to be lifted out of the packaging while the tab is connected to the packaging.

2. The boot remover according to claim 1, wherein the tab is attached to the packaging by a mechanical fixing and/or by an adhesive bond.

3. The boot remover according to claim 1, wherein the boot remover is substantially cylindrical for abutting and/or retaining the protective needle boot.

4. The boot remover according to claim 3, wherein the boot remover is arranged to engage the protective needle boot by friction and/or by at least one barb engageable in a recess or behind a shoulder on the protective needle boot.

5. The boot remover according to claim 1, comprising a flexible plastic material.

6. The boot remover according to claim 1, wherein the tab comprises a distal end part with an increased width for engaging in a front clearance distally from a constriction in the packaging.

7. A drug delivery arrangement comprising:
a drug delivery device for dispensing a dose of a drug, the drug delivery device comprising:
a support body having a first end defining a first opening and a second end defining a second opening,
a syringe barrel sealed by a stopper slidably disposed therein along an axial direction and adapted to have an integrated needle or to be coupled with a needle assembly comprising a needle, wherein the syringe barrel is positioned within the support body,
a protective needle boot arrangeable over the needle on the syringe barrel,
a needle shield adapted to be coupled to one of the first and second ends of the support body and slidably disposed thereon for covering or exposing the needle; and
a boot remover configured to engage the protective needle boot when attached to the drug delivery device, wherein the boot remover comprises a tab extending in a distal direction, wherein the tab is integrally shaped with a packaging of the drug delivery device, and wherein the boot remover is arranged to engage the protective needle boot,
wherein the packaging is arranged to allow a part of the drug delivery device proximally from the needle shield to be gripped while preventing access to the needle shield, wherein the packaging comprises a flexible material and is arranged as a blister pack, and wherein the tab of the boot remover is fixed to a distal end of the packaging;
wherein the packaging comprises a predetermined breaking point facilitating the packaging to be torn apart such that a proximal end of the drug delivery device is exposed and the entire needle shield is covered by the packaging.

8. The drug delivery arrangement according to claim 7, wherein the packaging comprises a deep-drawn rigid or flexible material.

9. The drug delivery arrangement according to claim 7, wherein the packaging is shaped corresponding to the drug delivery device with a rear clearance allowing to grip a part of the drug delivery device proximally from the needle shield whilst preventing access to the needle shield.

10. The drug delivery arrangement according to claim 7, wherein the boot remover is arrangeable over the needle shield to receive and substantially cover the needle shield.

11. The drug delivery arrangement according to claim 7, wherein the syringe barrel contains a pharmaceutically active compound.

12. A drug delivery arrangement comprising:
a drug delivery device for dispensing a dose of a drug, the drug delivery device comprising:

a support body having a first end defining a first opening and a second end defining a second opening, a syringe barrel sealed by a stopper slidably disposed therein along an axial direction and adapted to have an integrated needle or to be coupled with a needle assembly comprising a needle, wherein the syringe barrel is positioned within the support body, a protective needle boot arrangeable over the needle on the syringe barrel, a needle shield adapted to be coupled to one of the first and second ends of the support body and slidably disposed thereon for covering or exposing the needle; and a boot remover configured to engage the protective needle boot when attached to the drug delivery device, wherein the boot remover comprises a tab extending in a distal direction, wherein the tab is integrally shaped with a packaging of the drug delivery device, and wherein the boot remover is arranged to engage the protective needle boot, wherein the tab comprises a transversally arranged live hinge for such that a proximal end of the drug delivery device is configured to be lifted out of the packaging while the tab is connected to the packaging, wherein the packaging is arranged to allow a part of the drug delivery device proximally from the needle shield to be gripped while preventing access to the needle shield, wherein the packaging comprises a flexible material and is arranged as a blister pack, and wherein the tab of the boot remover is fixed to a distal end of the packaging.

* * * * *

UNITED STATES PATENT AND TRADEMARK OFFICE
CERTIFICATE OF CORRECTION

PATENT NO. : 10,653,850 B2
APPLICATION NO. : 15/037900
DATED : May 19, 2020
INVENTOR(S) : Chris Ward et al.

Page 1 of 1

It is certified that error appears in the above-identified patent and that said Letters Patent is hereby corrected as shown below:

On the Title Page

Column 1, Line 1 of "Inventors:", delete "Dennbigshire" and insert -- Denbighshire --

In the Claims

Column 13, Line 22, Claim 12, after "hinge", delete "for"

Signed and Sealed this
Seventh Day of July, 2020

Andrei Iancu
*Director of the United States Patent and Trademark Office*

SEQUENCE LISTING

```
<160> NUMBER OF SEQ ID NOS: 1

<210> SEQ ID NO 1
<211> LENGTH: 39
<212> TYPE: PRT
<213> ORGANISM: Artificial
<220> FEATURE:
<223> OTHER INFORMATION: Exendin-4(1-39), insulin analogue or derivative

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```